(12) United States Patent
Ding

(10) Patent No.: US 6,547,806 B1
(45) Date of Patent: Apr. 15, 2003

(54) VASCULAR SEALING DEVICE AND METHOD OF USE

(76) Inventor: Ni Ding, 4365 Juneau La., Plymouth, MN (US) 55446

(*) Notice: Subject to any disclaimer, the term of this patent is extended or adjusted under 35 U.S.C. 154(b) by 0 days.

(21) Appl. No.: 09/498,542

(22) Filed: Feb. 4, 2000

(51) Int. Cl.$^7$ ............................................. A61B 17/04
(52) U.S. Cl. .................................................... 606/213
(58) Field of Search ................................. 606/139, 213

(56) References Cited

U.S. PATENT DOCUMENTS

| | | | | |
|---|---|---|---|---|
| 3,874,388 A | * | 4/1975 | King et al. ................. | 606/213 |
| 4,744,364 A | | 5/1988 | Kensey ........................ | 128/334 |
| 4,873,978 A | | 10/1989 | Ginsburg .................... | 128/345 |
| 4,890,612 A | | 1/1990 | Kensey ........................ | 606/213 |
| 5,011,488 A | | 4/1991 | Ginsburg .................... | 606/159 |
| 5,021,059 A | | 6/1991 | Kensey et al. ............... | 606/213 |
| 5,370,660 A | | 12/1994 | Weinstein et al. ........... | 606/215 |
| 5,391,183 A | | 2/1995 | Janzen et al. ................ | 606/213 |
| 5,443,481 A | | 8/1995 | Lee ............................. | 606/213 |
| 5,674,231 A | | 10/1997 | Green et al. ................ | 606/142 |
| 5,690,674 A | | 11/1997 | Diaz ........................... | 606/213 |
| 5,707,393 A | | 1/1998 | Kensey et al. ............... | 606/213 |
| 5,728,122 A | | 3/1998 | Leschinsky et al. ......... | 606/213 |
| 5,728,132 A | | 3/1998 | Van Tassel et al. ......... | 606/213 |
| 5,853,421 A | | 12/1998 | Leschinsky et al. ......... | 606/213 |
| 5,868,778 A | | 2/1999 | Gershony et al. ........... | 606/194 |
| 5,951,583 A | | 9/1999 | Jensen et al. ................ | 606/194 |
| 5,957,952 A | | 9/1999 | Gershony et al. ........... | 606/213 |
| 5,986,043 A | | 11/1999 | Hubbell et al. ............. | 528/354 |
| 6,004,547 A | | 12/1999 | Rowe et al. ............. | 424/78.04 |
| 6,004,573 A | | 12/1999 | Rathi et al. ................. | 424/426 |
| 6,171,329 B1 | * | 1/2001 | Shaw et al. ................. | 606/213 |

* cited by examiner

*Primary Examiner*—Gary Jackson
(74) *Attorney, Agent, or Firm*—Shumaker & Sieffert, PA

(57) ABSTRACT

A collapsible medical device for use, e.g., as a vascular sealer. The device includes a sheath adapted to be positioned such that a distal end thereof is adjacent the opening. A mandrel is disposed within a lumen of the sheath and is adapted to be positioned such that a distal length thereof is adjacent the distal end of the sheath. A collapsible sealing member comprises a fluid-impervious film carried by a plurality of wires. The wires are attached to the mandrel and expand radially outward therefrom. In one method of using such a device, the sealing member is held in a collapsed position within the sheath. The sealing member is advanced through the sheath and beyond the distal end thereof, whereby the sealing member resiliently expands. The sealing member is positioned against the inner wall of the blood vessel adjacent the opening, thereby affecting a temporary seal of the opening. The sealant is introduced into the tissue tract. After hardening, the sealing member is collapsed within the sheath. The sheath the sealing member collapsed therein (together with any existing introducer) are then withdrawn proximally from the patient.

14 Claims, 8 Drawing Sheets

VASCULAR SEALING DEVICE AND METHOD OF USE

FIELD OF THE INVENTION

The present invention relates generally to medical devices. More particularly, this invention provides a hemostatic device used to seal percutaneous blood vessel punctures or incisions.

BACKGROUND

A wide variety of medical procedures are currently performed intravascularly. Such procedures commonly involve the insertion of various medical instruments, such as catheters, into an artery. For example, in the treatment of vascular disease, balloon catheters and the like have traditionally been inserted into an artery to perform procedures therein. To facilitate such procedures, a percutaneous puncture is generally formed in the affected artery or at a peripheral location (e.g., in the femoral artery).

Commonly, an introducer sheath is inserted into the artery first. Thereafter, the medical instrument itself is inserted through the sheath and is advanced to the affected portion of the artery. After the procedure has been completed, the instrument and sheath must be withdrawn from the artery. At this stage, bleeding through the percutaneous puncture must be stopped.

Traditional methods for closing the puncture commonly involve sutures and/or the application of prolonged manual pressure to the puncture site. For example, a physician or assistant might apply digital pressure over the puncture site until hemostasis has occurred and bleeding is stopped. This can be inconvenient, as it customarily takes a considerable amount of time before the puncture is effectively closed. While pressure must commonly be applied for at least half an hour, it frequently takes much longer. Further, the application of pressure can reduce the flow of blood through the affected artery, which can cause further complications. Finally, this method can result in less than ideal wound closures which can unexpectedly reopen long after closure is apparently complete. Accordingly, patients are typically restricted to bed rest for long periods after closure, in many cases for as long as 24 hours or longer.

Attempts have been made to provide devices and methods that overcome the limitations of such traditional closure methods. For example, Kensey's U.S. Pat. Nos. 4,744,364, 4,852,568, 4,890,612, 5,021,059, and 5,935,147 (the teachings of each of which are incorporated herein by reference) disclose similar devices and methods wherein a bioresorbable anchor is inserted through a percutaneous puncture in an artery. A tubular member containing the anchor is inserted through the opening in the artery so the distal end of the tubular member extends into the artery. The expandable anchor is then ejected into the artery through an opening in the distal end of the tubular member. A filament attached to the anchor is then pulled generally away from the artery until the anchor is pulled against the inside wall of the artery. A collagen sponge is then delivered to the puncture track, whereafter the wound is sutured closed. Thus, once the anchor member is deployed in the artery, it is never removed. Such a method seems less than ideal. For example, if the anchor is not properly deployed in the artery, then it may obstruct blood flow through the artery, compromising vessel patency. It would be more desirable to provide a vascular closure method where nothing remains in the artery after wound closure.

Several researchers have proposed methods and devices to achieve that end. U.S. Pat. Nos. 5,868,778 and 5,957,952 (both issued to Gershony et al.), and U.S. Pat. No. 5,951,583, (issued to Jensen et al.), disclose similar methods and devices for sealing percutaneous punctures using a balloon catheter. These references involve the insertion of the catheter into the artery until the balloon near the distal end of the catheter is positioned within the bloodstream. The balloon is then expanded and pulled against the interior wall of the artery at the puncture site, thereby temporarily closing the puncture. A liquid procoagulant is then introduced into the tissue track that extends through the tissue overlying the artery. Once hemostasis occurs, the balloon is deflated and the entire device is withdrawn from the artery. Unfortunately, there appears to be an appreciable risk that the balloon may rupture. This could leak procoagulant into the bloodstream, which could result in blood clotting and vascular occlusion in the patient's circulatory system.

U.S. Pat. Nos. 5,391,183; 5,591,204; 5,725,498; and 5,948,425, all issued to Janzen et al., and U.S. Pat. Nos. 5,853,421 and 5,728,122, issued to Leschinsky et al., suggest sealing arterial punctures by applying a plug of hemostatic material to the outside wall of a punctured artery. In the first step of one described method, the distance between the skin and artery is measured. A dilator and sheath may then be advanced to the measured depth. Alternatively, they may be advanced until they press upon the artery wall (whereupon increased resistance is felt). A collagen plug is then advanced toward the artery until it abuts the outer wall of the artery and overlaps the puncture on all sides. If the depth of the vascular track has not been properly measured, then over-deployed collagen might be dislodged to blood stream. This could result in blood clotting and vascular occlusion in the patient's circulatory system. The latest version of the device uses a J-locator to determine the tissue depth, which eliminates the need for a measurement. Still, the procedure seems complicated.

SUMMARY OF THE INVENTION

The present invention provides a vascular sealing device and a sealant for closing a puncture, incision, or other opening in the wall of a blood vessel. The invention also includes a method for closing such openings.

One embodiment of the present invention provides a vascular sealing device. The device includes a sheath that can be positioned so a distal end thereof is adjacent the opening. A solid mandrel is disposed within a lumen of the sheath. A collapsible sealing member having a fluid-impervious film carried by a plurality of wires is attached to the mandrel.

In another aspect of this invention, sealant is introduced to an area adjacent an opening in a blood vessel. The sealant may be introduced by flowing it into position. The sealant may be syringe injected. Alternatively, the sealant may be introduced by delivering it from a tampon. The sealant introduced may be a procoagulant. A thermally reversible material may be used as the sealant. The sealant may alternatively be a photo-initiated material. A second material may be brought into contact with the sealant to cause an in situ crosslink reaction, whereby the sealant and the second material begin to solidify.

In accordance with yet another embodiment, the present invention provides a method for closing an opening in a blood vessel of a patient. The method comprises providing a collapsible sealing member mounted on a mandrel. The sealing member has a naturally expanded configuration. A sheath with a distal end adjacent the opening in the blood vessel is also provided. The sheath has a lumen that is smaller than the expanded sealing member so the sealing member is kept in a collapsed position when it is inside the sheath. The sealing member is advanced through the sheath and beyond to its distal end, whereby it resiliently expands. The sealing member is then positioned against the inner wall of the blood vessel adjacent the opening to affect a temporary seal of the opening. A procoagulant is then introduced to an area adjacent the opening. Finally, the sealing member is collapsed within the sheath and withdrawn from the patient along with the sheath.

DETAILED DESCRIPTION

Figure 1:
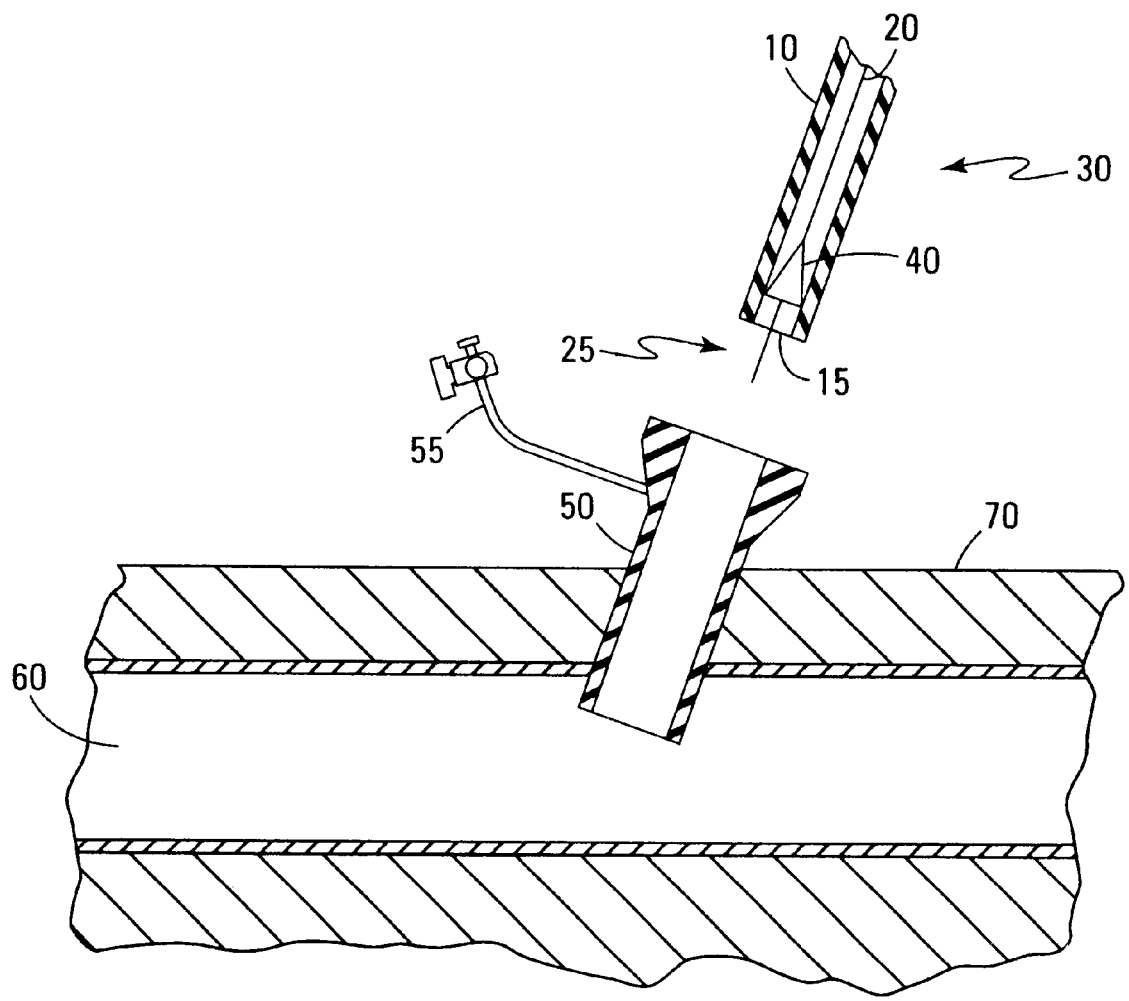
FIG. 1 is a schematic cross sectional illustration of a device according to one embodiment of the invention being inserted into a vessel.

FIG. 1 shows a vascular sealing device 30 according to one embodiment of the present invention. This sealing device 30 generally includes a sealing member 40, a mandrel 20, and a sheath 10. The device is particularly well suited for use in closing a puncture, incision, or other opening in the wall of a blood vessel. While the following discussion focuses on treating a human being, those skilled in developing or using such devices would appreciate that the device may also be used in treating other living beings. It should also be understood that, while the device is ideally suited to close openings in blood vessels, the device could also be used to close other types of openings within the body. Given the present teachings, one of skill in the art will recognize the utility of the device for other more diverse applications.

The discussion herein typifies use of the device to close openings of the size that commonly result from typical intravascular medical procedures. However, since the dimensions of the device depend on the size of the opening to be closed, it should be understood that the dimensions of the device may be greater or less than those discussed herein. Thus, where uncommonly large or small openings are to be closed (e.g., in pediatric applications), the sealing device used will have dimensions that fall outside the common ranges exemplified herein.

FIG. 1 depicts the vascular sealing device 30 as it is about to be inserted into an introducer 50 (As will be discussed later, the device 30 can be used with or without an introducer 50). The collapsible sealing member 40 shown in FIG. 1 is held in a collapsed position within a central lumen of the sheath 10. The sheath 10 is an elongated tubular member having an outlet formed at its distal end 15. The sheath 10 is dimensioned to fit within the introducer 50 and to extend from outside the patient's body to the opening in the blood vessel. Where an introducer 50 is used, the sheath 10 has a sufficiently small outside diameter to be inserted through the introducer 50. Where the device is used without an introducer, the diameter of the sheath 10 will depend on the size of the tissue tract (80, best seen in FIG. 4) extending from the opening in the blood vessel 60 to the patient's skin 70. That is, the outside diameter of the sheath 10 should be small enough that it can be inserted through the tissue tract 80 toward the opening in the blood vessel 60 without undue effort or trauma to the tissue adjacent the tract.

The dimensions of the sheath 10 will also depend on the dimensions of the sealing member 40. A central lumen of the sheath 10 is large enough to contain the collapsed sealing member 40, yet is smaller than the fully expanded sealing member 40. Desirably, the diameter of the sheath is as small as possible, so that when the device is removed from the patient, bleeding is minimized through the device's path of egress. As is more thoroughly discussed below, when the device 30 is ultimately removed from the patient, the path of egress is desirably small enough that the sealant in the tissue tract 80 will have a tendency to collapse around, and close, this path.

The sheath 10 can be formed of any suitable semi-flexible material. Desirably, the sheath is somewhat flexible, yet has a sufficient rigidity that it can be advanced through the introducer 50 or tissue tract 80 by an operator manipulating a proximal end of the sheath. The sheath 10 may be formed of hypotubing or a similar material. For example, the sheath may be constructed of stainless steel. Alternatively, it may be formed of a polymeric material. Other specific examples of materials that might be used include polyolefin, polycarbonate, polyimide, polyether, urethane, polyethelene (low density, high density, or linear low density), acrylic polymer, polytetrafluorosethylene (PTFE), polyesters (e.g., polyethylene teraphathalate), polyether and polyester block copolymers (e.g., Hytrel and Arnitel), nylon family materials, polyamide and polyether block copolymers (e.g., PEBAX), ethylene-vinyl acetate, and polyvinyl chloride. Preferably, the sheath comprises PEBAX, Arnitel, or Hytrel. Polyamide and polyether block copolymers are commercially available under the trade name PEBAX from Atochem North America, Inc., Philadelphia, Pa., U.S.A. Polyester/polyether block copolymers are sold commercially under the trade name Arnitel by DSM Engineering Plastic Products, which is located in Reading, Pa., U.S.A. Hytrel copolymers are commercially sold by E.l. Dupont de Nemours & Co., Wilmington, Del., U.S.A.

In one embodiment of the present invention, an outer surface of the sheath 10 has a lubricious coating or liner to facilitate the advance and withdrawal of the sheath during use. Such an exterior coating will reduce the friction between the sheath 10 and the introducer 50 or between the sheath 10 and the tissue in the tissue tract 80. If desired, an inner surface of the sheath 10 may also have such a coating or liner to facilitate movement of the sealing member 40 through the sheath 10. Such an interior coating or liner will reduce the friction between the sealing member 40 and the interior of the sheath 10. In a preferred embodiment, a lubricious coating or liner is disposed on both the outer and inner surfaces of the sheath. Any suitable lubricious coating or liner can be used. For example, a PTFE liner may be used. Alternatively, a hydrophobic silicone coating or any commercially available lubricious hydrophilic coating may be used. In a particularly preferred embodiment, silicone coating is provided on inner and outer surfaces of the sheath.

Figure 2:
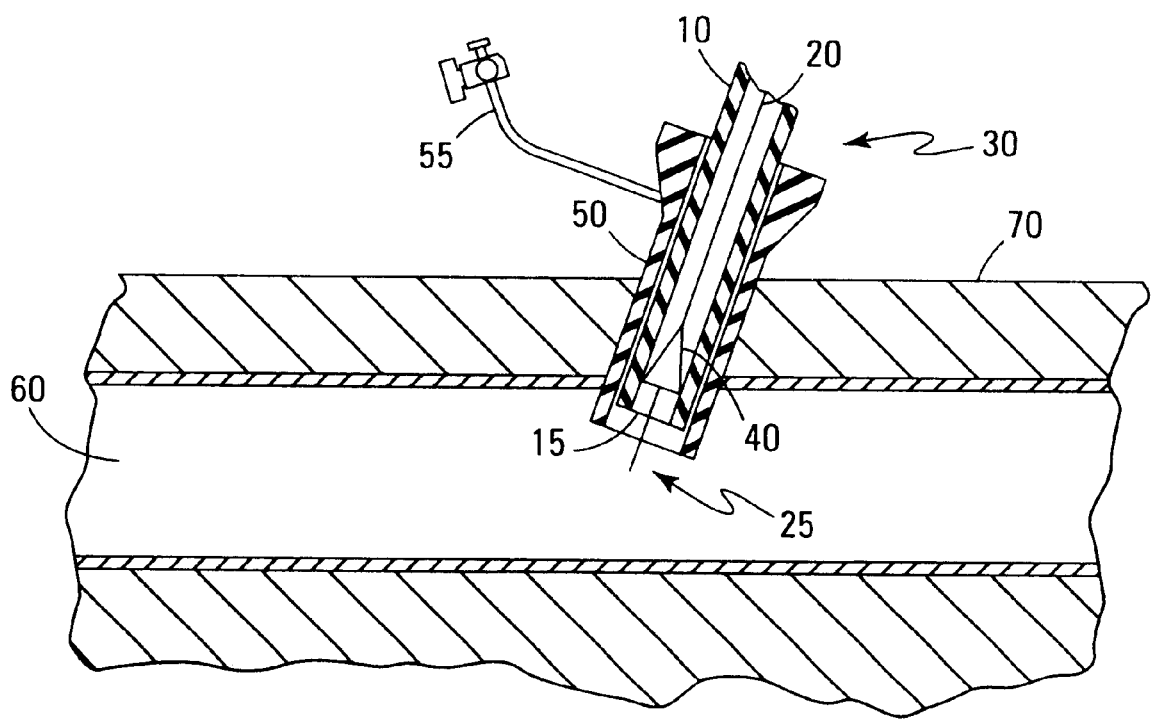
FIG. 2 is a schematic illustration of the device shown in FIG. 1 with a sealing member advanced into an introducer.
Figure 3:
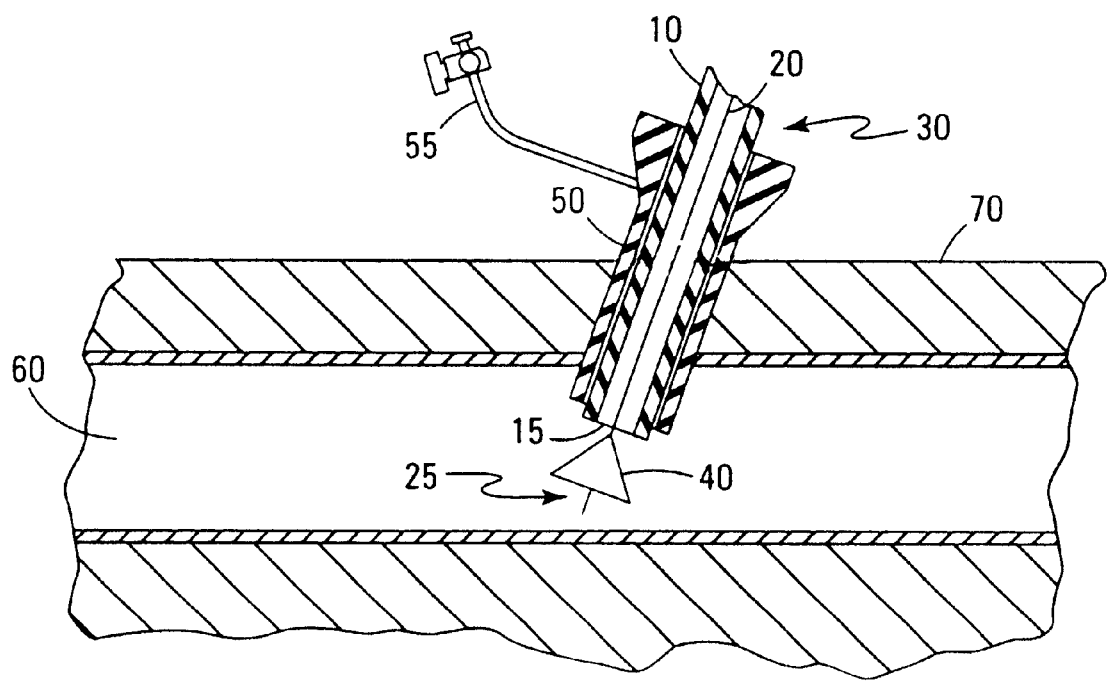
FIG. 3 is a schematic illustration of the same device after the sealing member has been deployed.

The sealing member 40 is a collapsible member which is sufficiently compact to fit within the central lumen of the sheath 10 when compressed, contracted, or otherwise collapsed (see FIGS. 1 and 2). When the sealing member 40 is unconstrained, however, it takes on a naturally expanded configuration (see FIGS. 3 and 4) suitable for closing the opening in the blood vessel. As is best seen perhaps with reference to FIG. 6, the sealing member 40 of this embodiment comprises a plurality of wires 47 (The terms "wire" and "wires" are used herein to mean any slender elongated member, without regard to composition). In a preferred embodiment, the wires 47 have a generally round cross-sectional shape. If desired, though, one or more of the wires 47 may have a cross-sectional shape that is generally square, rectangular, or triangular. For example, in one embodiment, at least one wire 47 is flattened and has a generally rectangular cross-sectional shape, configured with one of its wider faces oriented toward the interior of the sealing member. If desired, all of the wires 47 may be flattened in this manner. Furthermore, each wire need not be regular along its entire length. If desired, at least one of the wires can be twisted, serpentine, or otherwise irregular.

The wires 47 can be formed of any suitable resilient material. Various metals, such as stainless steel, or metal alloys can be used. Alternatively, any suitable polymeric material could be used (such as carbon fiber-reinforced biocompatible resin).

In another embodiment, the wires 47 are formed of a non-degradable polymer fiber (such as polyethylene teraphathalate). If desired, though, the wires may be formed of a degradable material (such as poly-l-lactic acid). In a preferred embodiment, the wires 47 are formed of a super elastic, shape memory alloy. In a particularly preferred embodiment, the wires 47 comprise Nitinol or Elgiloy.

Figure 5:
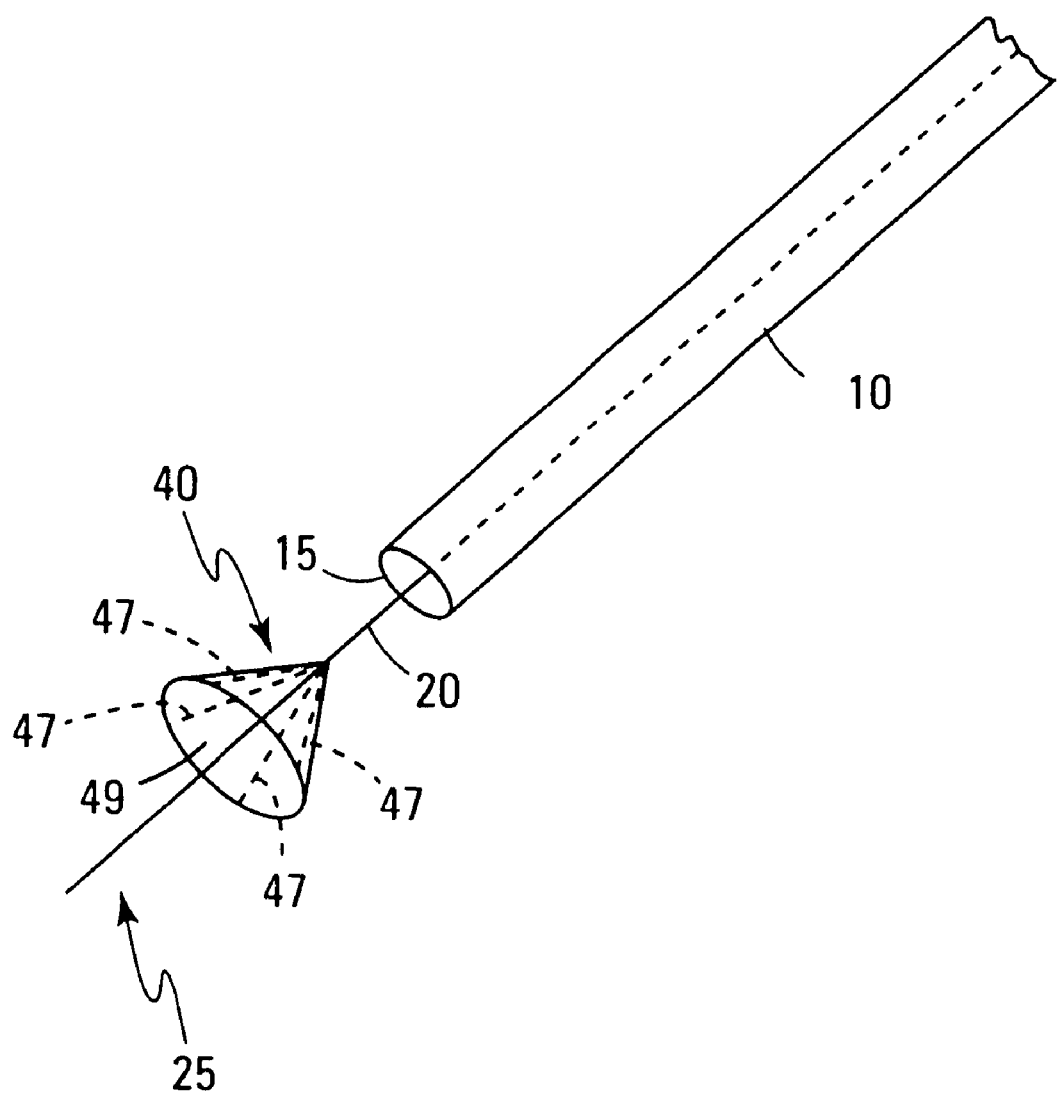
FIG. 5 is a perspective view of the sealing member shown in FIG. 4.

As is best seen with reference to FIG. 5, the sealing member 40 is carried by a mandrel 20. If desired, an outer surface of the sealing member 40 and/or the mandrel 20 may be provided with a lubricious coating (such as the coatings suggested above with reference to the inner and outer surfaces of the sheath) to facilitate manipulation through the sheath 10.

The sealing member 40 may be soldered, welded, or glued to the mandrel 20. For example, any suitable eutectic braze can be used. A single end of the sealing member 40 may be attached to the mandrel 20. For example, in the embodiment shown in FIG. 5, the apex of the generally conical sealing member 40 defined by the expanded wires 47 is attached to the mandrel 20 at a location spaced proximally of the mandrel's distal end. If desired, though, both ends of the sealing member may be attached to the mandrel 20. In one embodiment (not shown), a proximal end of the sealing member is fixedly attached to the mandrel, while a distal end of the sealing member is slidably attached to the mandrel. In another embodiment (not shown), a proximal end is slidably attached, while a distal end is fixedly attached. The sealing member could also be attached to the mandrel other than at the ends of the sealing member. In one such embodiment (not shown), the middle of the sealing member is mounted to the mandrel. In sum, virtually any desired attachment between the mandrel and the sealing member will suffice so long as the sealing member is secured to the mandrel yet remains free to expand and collapse (as discussed below).

The mandrel 20 can be any suitable wire. Conventional guidewires can be used. For example, commercially available 0.14" or 0.35"–0.38" guidewires could be used. If desired, the guidewire can be provided with a diameter that varies along its length. For example, to reduce the profile of the device, it may be desirable to have a smaller diameter in the region where the sealing member 40 is constrained.

In the embodiments illustrated in FIGS. 1–6, a distal length 25 of the mandrel 20 extends distally beyond the sealing member. This is desirable in that it facilitates the user's ability to maneuver the device inside the patient. As is well known in the art, guidewires are commonly provided with an atraumatic distal length (typically including a flexible helical coil) which may be straight or curved in its natural state. This structure is known to reduce the level of trauma caused in maneuvering such devices within the body.

The wires 47 of the sealing member 40 may alternatively be attached to the mandrel 20 so the distal length 25 of the mandrel 20 does not extend beyond the distal end of the sealing member 40. In one embodiment (not shown), the wires 47 of the sealing member 40 are attached to the distal tip of the mandrel 20. Such a configuration reduces the profile of the device. In this embodiment, the ends of the wires 47 are optionally provided with atraumatic tips.

The sealing member 40 has a naturally expanded configuration, yet may be collapsed in use. In the embodiments shown in FIGS. 5 and 6, the sealing member is attached at one end to the mandrel 20 and expands radially outward therefrom. In these embodiments, the wires are biased so they assume an expanded configuration when unconstrained. This bias may be derived from the inherently resilient character of the wire material itself, with the wires resiliently expanding toward the expanded configuration when the constraint is removed. That is, the wires may be attached to the mandrel in an outwardly diverging manner. Alternatively, one or more separate biasing members (not shown) may be provided to urge the wires toward an expanded configuration. In one embodiment (not shown), the wires are attached to the mandrel in an unbiased manner and a resilient ring is carried on the mandrel beneath the wires, urging the wires toward an expanded configuration, yet buckling to permit the wires to be urged inwardly into a more compact configuration for delivery.

In the embodiments illustrated in FIGS. 1–6, the wires of the unconstrained sealing member assume a naturally expanded configuration that is generally conical. As will be obvious to one of skill in the art, the wires may be bent in their natural, unconstrained shape. For example, the wires of the sealing member may be biased toward a naturally expanded configuration that is generally dome-shaped. Alternatively, the wires may be shaped to form a pyramid when unconstrained. In another embodiment (not shown), the wires of the sealing member assume a naturally expanded configuration that is generally spherical. In still another embodiment (not shown), the wires of the sealing member assume an unconstrained configuration having a generally diamond-shaped cross section (along an axis defined by the mandrel).

Figure 6:
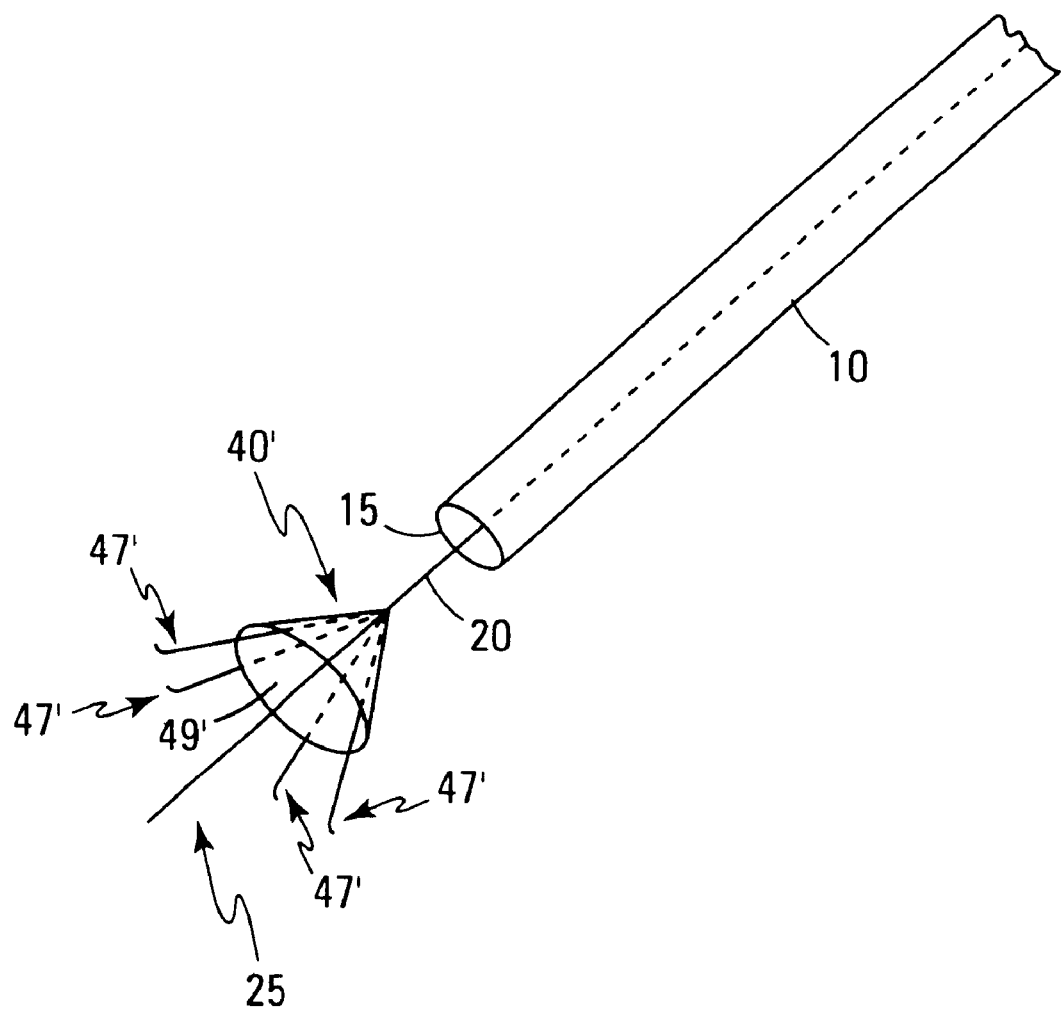
FIG. 6 is a perspective view of a sealing member according to another embodiment of the present invention.

In the embodiments illustrated in FIGS. 5 and 6, the sealing member comprises a frame formed of four wires. If desired, the sealing member may be constructed of a larger or smaller number of wires. For example, in another embodiment (not shown), the frame of the sealing member is constructed of six spaced-apart wires. In still another embodiment (not shown), the frame is formed of only three wires. In the embodiment illustrated in FIG. 5, the wires 47 are spaced apart in a generally equiangular fashion. If desired, though, the wires of the sealing member may be spaced apart in an irregular manner.

The wires 47 of the sealing member 40 illustrated in FIG. 5 are generally straight. If desired, though, the wires of the sealing member may bend radially outward near their tips. Such a bend may provide better anchoring against the interior wall of the blood vessel when the sealing member is positioned to seal the opening in the blood vessel. Preferably, the wires of the sealing member do not extend distally beyond the distal edge of a film (discussed below) carried on the wires. For example, the wires 47 of the sealing member 40 illustrated in FIG. 5 do not extend beyond the distal edge of the film 49. However, if desired, the wires of the sealing member may extend beyond the distal edge of the film. For example, in the embodiment shown in FIG. 6, all four of the wires 47' extend beyond the distal edge of the film 49'.

Figure 7:
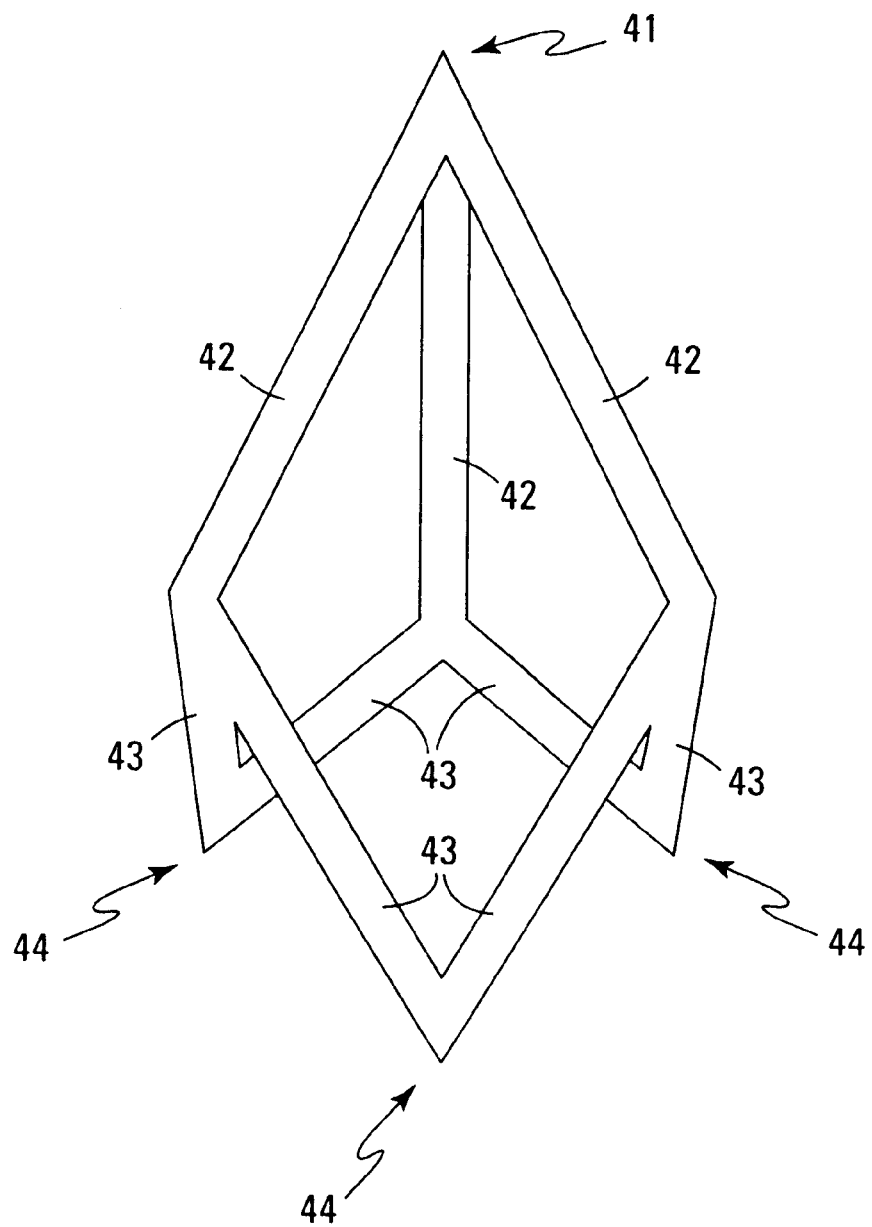
FIG. 7 is a side view of a sealing member according to a different embodiment of the present invention.

FIG. 7 illustrates another embodiment of the present invention wherein the wire frame is more intricate. In this embodiment, the wire frame defines a pyramid-like configuration with three diamond-shaped sides. Three primary wires 42 extend radially outward from the apex 41, which is preferably the point of attachment to the mandrel 20 (not shown). Six secondary wires 43 form the distal portion of the frame, which terminates at three distal corners 44. Optimally, the distal corners 44 are bent radially outward (not shown) to provide better anchoring against the interior wall of the blood vessel.

Figure 8:
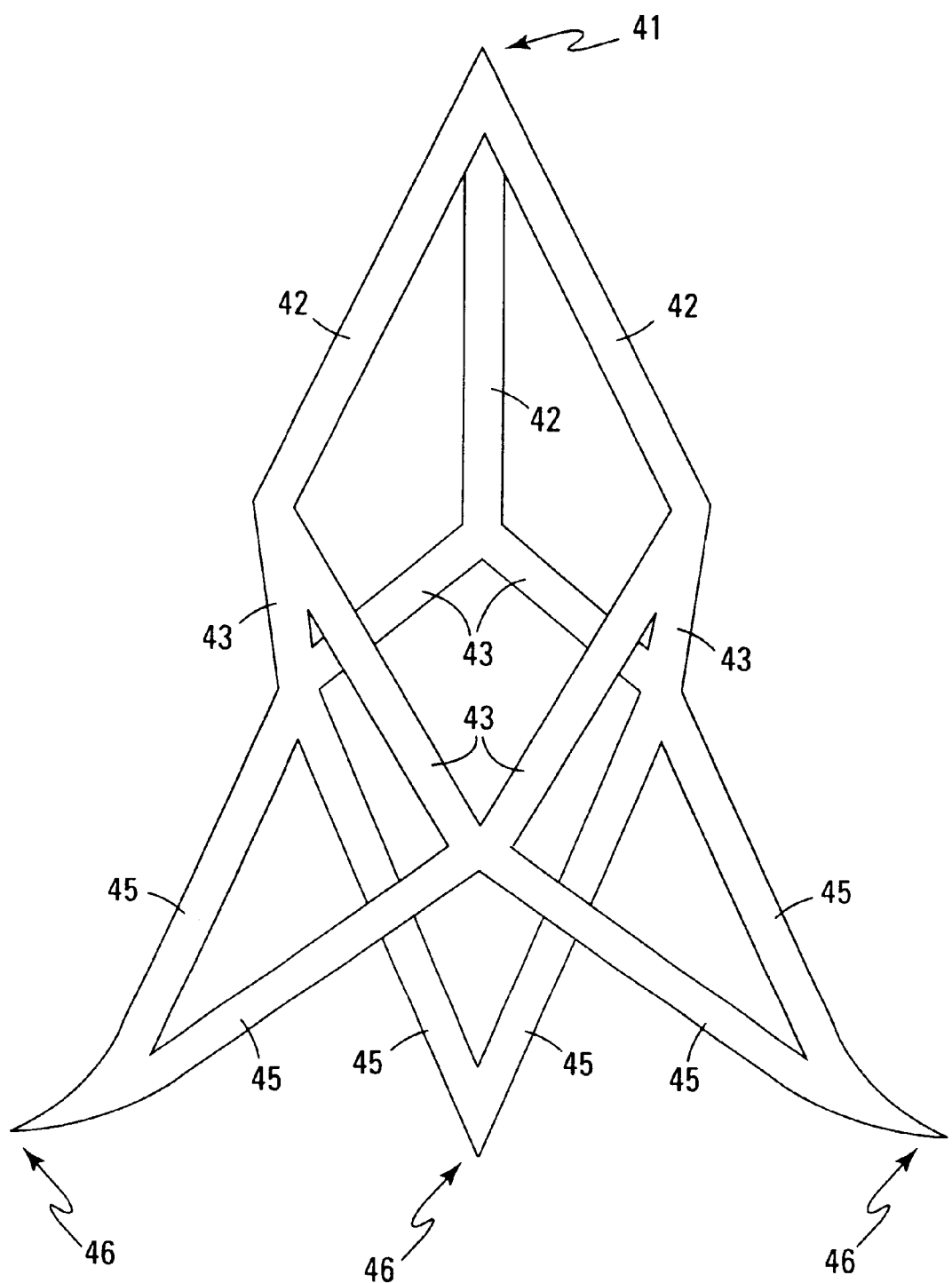
FIG. 8 is a side view of a sealing member according to another embodiment of the present invention.

FIG. 8 illustrates another embodiment wherein an intricate wire frame is provided. In this embodiment, the wire frame defines a proximal configuration with three generally diamond-shaped sides, and a distal configuration that resembles a crown. Three primary wires 42 and six secondary wires 43 define the diamond-shaped sides of the proximal portion of the frame. Six tertiary wires 45 form the generally crown-shaped distal portion of the frame. The distal portion of the frame terminates at three distal corners 46, which are bent radially outward.

As is best seen perhaps with reference to FIG. 5, the wires 47 of the sealing member 40 carry a film 49. The film is substantially fluid-impervious so that when the sealing member is positioned against the inner wall of the blood vessel adjacent the opening therein, passage of blood and procoagulent through the film will be blocked, or at least greatly curtailed. Desirably, the film is elastic in nature so it will not unduly interfere with the self-expanding properties of the sealing member. If desired, though, the film can be formed of a semi-elastic material. Such a semi-elastic film is desirably sized so it will be taut when the sealing member is expanded, and it may be pleated in a fan-like fashion when the sealing member is in a collapsed configuration prior to deployment.

The film can be formed of any suitable fluid-impervious material. Examples of materials that can be used include natural or synthetic rubber, polyolefin, polycarbonate, polyimide, polyether, urethane, silicone, polyethelene (low density, high density, or linear low density), acrylic polymer, polytetrafluorosethylene (PTFE), polyester (e.g., polyethylene teraphathalate), polyether and polyester copolymers (e.g., Hytrel and Arnitel), nylon family materials, polyamide and polyether block copolymer (e.g., PEBAX), ethylene-vinyl acetate, and polyvinyl chloride. Other acceptable materials would be apparent to one of skill in the art. In a preferred embodiment, the film comprises urethane.

The film can be applied to the wires of the sealing member by any suitable coating method. For example, the film may be dip coated, spray coated, or wrapped onto the wires of the sealing member. The film can be applied before or after the sealing member is disposed on the mandrel. If desired, the film can be formed into a particular shape and then attached to the wires with glue or the like. Optionally, an antithrombogenic coating is applied to the side of the film that will engage the inner wall of the blood vessel. This may reduce the likelihood that thrombii will be formed and dislodged into the bloodstream during manipulation of the device. In a preferred embodiment, this coating comprises heparin.

The manner in which the device 30 can be used is schematically illustrated with reference to FIGS. 1–4. Prior to use of the device, the sealing member 40 is collapsed and inserted into the sheath 20. While this can be done manually by medical personnel just prior to performing a medical procedure, it would be desirable to provide the device 30 as a kit wherein the sealing member 40 has already been positioned within the sheath 20 (as shown in FIG. 1). Thus, the device 30 would arrive in a ready-to-use state. This may prevent delays in sealing an open blood vessel where medical staff would otherwise need to insert the sealing member 40 into the sheath 20 before using the device 30. If the sealing member and sheath are shipped separately, then the sealing member can be easily collapsed by inserting the mandrel in the distal end of the sheath and withdrawing it proximally. The distal edge of the sheath will engage the sealing member and further proximal movement of the mandrel can collapse the sealing member.

In a preferred method of the present invention, an introducer 50 is left in place within a patient following the completion of an intravascular medical procedure. As is seen in FIGS. 1 and 2, the device 30 is inserted, distal end first, into the proximal end of the existing introducer 50. The device 30 is then advanced through the introducer 50 and into the blood vessel 60. FIG. 2 illustrates one such device 30 as it is being advanced through the introducer 50.

In another method of the present invention (not shown), the device 30 is used without an introducer and is inserted directly into the tissue tract 80 above the opening in the blood vessel 60. The device 30 is then advanced through the tissue tract 80 and toward the blood vessel 60.

The device 30 is advanced toward the blood vessel 60, through either the introducer 50 or the tissue tract 80, until the distal end 15 of the sheath 10 is adjacent the opening in the blood vessel. If desired, the device 30 can be advanced until the distal end 15 of the sheath 10 is actually within the blood vessel 60. However, depending on the configuration of the sealing member 40, it may not be necessary to advance the device 30 this far. That is, it may be possible to deploy the sealing member 40 into the blood vessel 60 when the distal end 15 of the sheath 10 is adjacent the opening in the blood vessel 60, but within the tissue tract 80. For example, the configuration of the sealing member 40 may be such that it will extend distally beyond the sheath before it fully expands.

The sealing member 40 can be deployed into the blood vessel 60 once the device 30 is properly positioned adjacent the opening in the blood vessel. The sealing member 40 is deployed by moving the sheath 10 and the mandrel 20 relative to one another so the sealing member 40 emerges from the distal end 15 of the sheath 10. This is accomplished by manipulating the proximal end of the sheath 10 and/or the proximal end of the mandrel 20. For example, the user could urge the mandrel 20 toward the blood vessel 60, while holding the sheath 10 in a fixed position. Alternatively, the user could urge the sheath 10 away from the blood vessel 60, while holding the mandrel 20 in a fixed position. In any event, the sealing member 40 emerges from the distal end 15 of the sheath 10 as a result of the relative movement of the sheath 10 and the mandrel 20. As is, perhaps, best seen with reference to FIGS. 4 and 5, the sealing member 40 resiliently expands toward its naturally expanded configuration upon deployment from the sheath 10.

Figure 4:
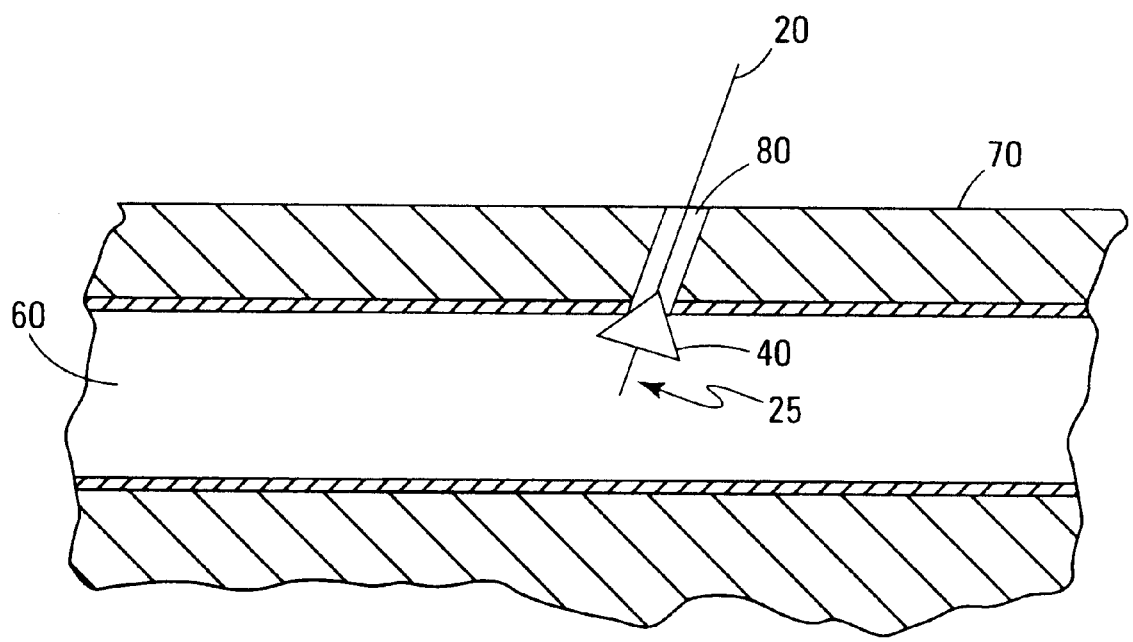
FIG. 4 is a schematic illustration of the same device with the sealing member placed against the inner wall of the blood vessel opening.

The sealing member 40 is then positioned against the inner wall of the blood vessel 60 adjacent the opening therein. This may be done by drawing the mandrel 20 proximally until the sealing member 40, which is inside the blood vessel 60, engages the blood vessel wall. The mandrel 20 and the introducer 50 may be drawn proximally as a unit until the sealing member 40 engages the inner blood vessel wall. The user will now the sealing member 40 is appropriately seated against the blood vessel wall when resistance is felt. FIG. 4 illustrates a sealing member 40 according to one embodiment of the present invention wherein the sealing member 40 has been positioned against the inner wall of the blood vessel 60 to form a temporary hemostatic seal, which is desirably maintained while the sealant is delivered to the tissue tract 80.

The user can secure the sealing member 40 in position while the sealant is delivered by physically holding the mandrel 20 in place. If desired, though, the mandrel 20 can be secured in position with any suitable fixation means. For example, any gripping device (such as a clamp or vice) may be used to hold the mandrel with respect to the patient or the introducer 50. Alternatively, a variety of gripping arrangements comprising adhesives may be used. If desired, though, a stopping and locking mechanism can be employed. For example, a stopper (not shown) mounted to the mandrel 20 could be positioned against the patient's skin so the sealing member 40 is held in position by resistance from the tissue between the stopper and the sealing member 40. In any event, the temporary seal formed by the sealing member 40 substantially prevents (or at least greatly curtails) fluid flow between the blood vessel 60 and the tissue tract 80.

Sealant is then delivered to the tissue tract 80. The amount of sealant delivered to the tissue tract 80 can be varied. For example, larger wounds will generally require more sealant. However, the user should provide enough sealant to bring about a substantial hemostatic closure of the wound. It is well within the ability of those skilled in the art to estimate the amount of sealant needed in a given case. Desirably, a substantial portion of the tissue tract 80 is filled with sealant. Optimally, the entire tissue tract 80 is filled with sealant.

It is preferable to use a sealant that will break down or degrade within the body to nontoxic components. Any suitable bioresorbable material may be used. Optimally, the sealant is a procoagulant. Procoagulants activate platelets in the blood and speed up the blood clotting process in a way that is well known in the art. When the sealant reaches the opening in the blood vessel 60, it is stopped from further advancement by the sealing member 40. Since the sealing member 40 is fluid impermeable, the sealant is kept from entering the blood vessel even if it is delivered in the form of a liquid.

The sealant can be inserted into the tissue tract 80 by various means. Preferably, the sealant is delivered in a flowable form. Where an introducer 50 has been used, the sealant may be delivered through a sidearm 55 of the introducer 50 (as is well known by skilled artisans). For example, the sealant may be syringe injected through the introducer 50. Where sealant is delivered through an introducer 50, the distal end of the introducer 50 should remain within the tissue tract 80 while the sealant is delivered. Desirably, the distal end of the introducer 50 is positioned just beneath the skin 70 during sealant delivery. Where no introducer is used, a syringe outside the patient can be used to deliver sealant directly through the tissue tract 80. In this case, a lumen communicating with the syringe and having an outlet adjacent the opening can be used to deliver the sealant.

The sealant can also be delivered to the tissue tract 80 in the form of a gel. In this case, it is desirable to remove the introducer 50 from the patient (if one has been used) and deliver the sealant using a bioresorbable tampon. For example, a mass of sealant may be pushed around the mandrel 20, along the tissue tract 80, and into position adjacent the opening in the blood vessel 60. The pusher portion of the tampon desirably has a central opening through which the mandrel is allowed to provide passage of the tampon along the mandrel 20.

The sealant may also be delivered in the form of a solid or paste. For example, a resilient sponge-like mass of sealant may be used. A collagen sponge can be used. Alternatively, the sponge or paste may comprise a collagen derivative, a collagen copolymer, a fibrin adhesive, or a hydrogel. For example, the sponge may comprise hyaluronan or its derivatives, optionally mixed with collagen. Where the sealant is a solid or paste, once any existing introducer 50 is removed, the sealant is inserted into the tissue tract 80 and advanced toward the blood vessel 60. Whether the sealant is delivered to the tissue tract 80 in the form of a liquid, gel, or solid, a substantial amount of the sealant is stopped from further advancement once it engages the sealing member 40. Thus, a substantial amount of the sealant is kept from entering the blood vessel.

In one aspect of the present invention, a thermally reversible material can be used as a sealant. These materials possess reverse thermal gelation properties. Preferably, at temperatures below a known gelation temperature the material is a liquid or a soft gel, but at temperatures above or at the gelation temperature the material begins to harden and may become a gel or a semi-solid. Optimally, the gelation temperature of the material is no higher than about 37° Celsius, whereby the material is delivered in the form of a liquid or soft gel, but begins to harden once at body temperature (about 37° Celsius for humans) inside the tissue tract 80.

A number of commercially available thermally reversible materials should be suitable. For example, triblock copolymers containing polypropylene oxide and polyethylene oxide should be suitable. Such materials are well known by skilled artisans in the field and are sold commercially under the trade name Pluronic by the BASF Corporation, Parsippany, N.J., U.S.A. Alternatively, triblock poly(lactide-co-glycolide) polyethylene glycol copolymers should also be suitable. Such materials are commercially available from MacroMed, Inc., which is located in Salt Lake City, Utah, U.S.A, under the trade name ReGel. The basic technology underlying the ReGel brand gels is discussed in U.S. Pat. No. 6,004,573 (the teachings of which are herein incorporated by reference). If desired, the gel can be formed of a graft copolymer of polyacrylic acid and Pluronic. Alternatively, a graft copolymer of Pluronic and chitosan can be used. Other suitable materials include Poly(N-isopropylacrylamide), and copolymers of polyacrylic acid and Poly(N-isopropylacrylamide).

Such materials provide a highly controllable sealant. By selecting a material that forms a liquid at room temperature, the sealant can be easily delivered through a conventional syringe. By providing a sealant with a gelation temperature no higher than about 37° Celsius (human body temperature), the user can assure that the material will begin to form a gel or a semi-solid immediately upon delivery to the tissue tract.

In another aspect of the present invention, a photo-initiated material can be used as sealant. Such a sealant may comprise a light sensitive polymerization initiator, which would preferably be delivered to the tissue tract in the form of a liquid. Once the liquid has been delivered to the tissue tract, a source of light having a proper activating wavelength is directed onto the liquid to initiate polymerization and/or a crosslink reaction. This causes the sealant to become non-fluent. For example, the sealant may become a solid gel. Photopolymerization is well known by skilled artisans in the relevant field. For example, U.S. Pat. No. 6,004,547 (the teachings of which are herein incorporated by reference) describes an apparatus and process for accomplishing photopolymerization with a variety of hydrogel polymers.

Any suitable photo-initiated material can be used. A number of to photopolymerizable hydrogels are commercially available. U.S. Pat. No. 5,986,043 (the teachings of which are herein incorporated by reference) discloses a number of photopolymerizable biodegradable hydrogels that should be suitable. Such materials are commercially available under the trade name FocalSeal from Focal, Inc., which is located in Lexington, Mass., U.S.A. The light source is selected to be of an appropriate activating wavelength to sustain, or at least initiate, polymerization and/or a crosslink reaction. The intensity of the light source is selected to achieve polymerization and/or a crosslink reaction within the desired time. Any suitable light directing mechanism can be used to deliver light to the sealant. For example, an optical fiber may be used.

In still another aspect of the present invention, a gelled sealant can be formed in the tissue tract by creating an in situ crosslink reaction in liquid delivered to the tissue tract. In this case, a liquid prepolymer and a liquid crosslink agent are delivered separately to the tissue tract. The prepolymer and the crosslink agent may be delivered to the tissue tract one after the other, or simultaneously through separate delivery lumens. In either case, the interaction of the prepolymer and the crosslink agent causes an in situ crosslink reaction, whereby the two liquids to begin to solidify. Such reactions would be readily understood by skilled artisans, as would the materials used therein. For example, the 2000 Shearwater Polymers, Inc. catalog discloses the reaction mechanism. Various suitable prepolymers and crosslink agents are commercially available from Shearwater Polymers, Inc., which is located in Hunstville, Ala., U.S.A. Preferably, the prepolymer comprises an amino group and the crosslink agent comprises a succinimidyl derivative.

The sealant may also be delivered to the tissue tract 80 in the form of a suspension. For example, a collagen and thrombin suspension can be used. In this case, thrombin promotes the formation of a fibrin clot, while collagen provides mechanical strength and also promotes clotting. Other PH sensitive, ionic strength sensitive materials may also be used.

The sealant may comprise a thrombin suspension containing bioresorbable polymer particles. These particles can be formed of a bioresorbable material such as polylactic acid, polyglycolic acid, copolymers of polylactic acid and polyglycolic acid, polycarprolactone, polylactic acid-polyethylene oxide, polyglycolic acid-polyethylene oxide copolymers, cellulose, starch, and/or alginate. Optimally, the particles are provided with irregular shapes to facilitate thrombosis formation.

Various other functional materials can also be delivered to the tissue tract. For example, in addition to the sealant, a fluorescent dye (such as those commonly used in cathetorization laboratories) can be added to the sealant to enhance fluoroscopic visibility. Where a mixable sealant is used, the dye could simply be mixed into the sealant composition. A variety of therapeutic agents may also be delivered to the tissue tract. In many cases, it may be desirable to add an antimicrobial agent to the sealant to reduce the likelihood of infection. For example, penicillin, cetoxitin, oxacillin, and gentamycin may be used. Other therapeutic substances might also be used. For example, it may be desirable to add anti-inflammatory agents, anti-oxidant agents, antimitotic agents, antiometabolite agents, or anti-restenosis agents. Various natural and synthetic biological agents may be added. For example, it may be desirable to add a procoagulant (e.g., thrombin), polypeptide, protein, or polynucleotide.

Depending on the sealant chosen, it may be necessary to wait a short period of time before the sealant forms a hemostatic closure within the tissue tract. Those skilled in the art will appreciate the necessity of this waiting period and will also be able to estimate the amount of time required for a particular sealant to hemostatically seal a particular opening. Once the sealant is ready and will itself serve as a hemostatic seal, the device 30 (along with any existing introducer 50) can be withdrawn from the blood vessel 60.

In order to withdraw the device 30 from the blood vessel 60, the operator may withdraw the mandrel 20 proximally while holding the sheath 10 in a fixed position until the sealing member 40 is once again collapsed inside the sheath 10. Alternatively, the operator may urge the sheath 10 distally while holding the mandrel 20 in a fixed position until the sealing member 40 is collapsed inside the sheath 10. Similarly, the operator may simultaneously withdraw the mandrel 20 proximally and urge the sheath 10 distally. In any case, the sealing member 40 will begin to collapse inside the sheath 10 when the distal edge of the sheath 10 engages the sealing member 40. This may be accomplished by manipulating the proximal ends of the sheath 10 and the mandrel 20. The sheath 10 and the collapsed sealing member 40 therein are then withdrawn from the blood vessel 60 and through the sealant until the device 30 is removed from the patient entirely.

A small lumen may remain along the path where the device 30 has been withdrawn. Desirably, the device 30 has such a small diameter that only a very small lumen, if any, will remain along this path of egress. The sealant in the tissue tract 80 will tend to collapse around, and close, this path. However, the application of compressive force should hemostatically seal such a small lumen. If it is desired to close this lumen more securely, then a surgical suture may be applied to the site of the wound. Preferably, a bioresorbable suture is used.

While a preferred embodiment of the present invention has been described, it should be understood that various changes, adaptations, and modifications can be made therein without departing from the spirit of the invention and the scope of the appended claims.

What is claimed is:

1. A vascular sealing assembly for closing an opening in a blood vessel, the assembly comprising:
   a) a sheath adapted to be positioned such that a distal end thereof is adjacent the opening in the blood vessel;
   b) a mandrel disposed within a lumen of the sheath, the mandrel being adapted to be positioned such that a distal length thereof is adjacent the distal end of the sheath;
   c) a collapsible sealing member comprising a fluid-impervious film carried by a plurality of wires, the wires being attached to the mandrel and expanding radially outward therefrom; and d) a sealant adapted for delivery to an area adjacent the opening in the blood vessel.

2. The vascular sealing assembly of claim 1 wherein the sealant is a procoagulent.

3. The vascular sealing assembly of claim 1 further including an introducer disposed around the sheath through which the sealant is adapted to be delivered to the area adjacent the opening.

4. The vascular sealing assembly of claim 1 further including a syringe for injecting the sealant to the area adjacent the opening.

5. The vascular sealing assembly of claim 1 wherein the wires are formed of stainless steel.

6. The vascular sealing assembly of claim 1 wherein the wires are formed of a shape memory alloy.

7. The vascular sealing assembly of claim 1 wherein the wires are formed of a metal alloy selected from the group consisting of Nitinol and Elgiloy.

8. The vascular sealing assembly of claim 1 wherein the wires are formed of polymeric fiber.

9. The vascular sealing assembly of claim 1 wherein the wires comprise carbon fiber.

10. The vascular sealing assembly of claim 1 wherein the film comprises a flexible material selected from the group consisting of urethane, silicone, rubber, and polyvinyl chloride.

11. A vascular sealing assembly for closing an opening in a blood vessel, the assembly comprising:

a) a sheath adapted to be positioned such that a distal end thereof is adjacent the opening in the blood vessel;

b) a mandrel disposed within a lumen of the sheath, the mandrel being adapted to be positioned such that a distal length thereof is adjacent the distal end of the sheath; and c) a single collapsible sealing member attached to the mandrel and having a generally conical expanded configuration, the sealing member comprising a fluid-impervious film carried by a plurality of wires expanding radially outwardly from the mandrel such that an apex of the expanded conical sealing member is proximal relative to an expanded large end of the sealing member.

12. The vascular sealing assembly of claim 11 wherein the distal ends of the wires have atraumatic tips.

13. A vascular sealing assembly for closing an opening in a blood vessel, the assembly comprising:

a) a sheath adapted to be positioned such that a distal end thereof is adjacent the opening in the blood vessel;

b) a mandrel disposed within a lumen of the sheath, the mandrel being adapted to be positioned such that a distal length thereof is adjacent the distal end of the sheath;

c) a collapsible sealing member comprising a fluid-impervious film carried by a plurality of wires, the wires being attached to the mandrel and expanding radially outward therefrom; and d) an introducer disposed around the sheath through which sealant is adapted to be delivered to the area adjacent the opening.

14. A vascular sealing assembly for closing an opening in a blood vessel, the assembly comprising:

a) a sheath adapted to be positioned such that a distal end thereof is adjacent the opening in the blood vessel;

b) a mandrel disposed within a lumen of the sheath, the mandrel being adapted to be positioned such that a distal length thereof is adjacent the distal end of the sheath;

c) a collapsible sealing member comprising a fluid-impervious film carried by a plurality of wires, the wires being attached to the mandrel and expanding radially outward therefrom; and d) a syringe for injecting sealant to the area adjacent the opening.

* * * * *